(12) United States Patent
Bertelsen et al.

(10) Patent No.: US 6,991,923 B2
(45) Date of Patent: Jan. 31, 2006

(54) PROCESS FOR MANUFACTURING OF TAGATOSE

(75) Inventors: Hans Bertelsen, Videbæk (DK); Kristian Eriknauer, Viby J (DK); Karen Bøttcher, Videbæk (DK); Hans Jørgen Singel Christensen, Videbæk (DK); Peter Stougaard, Skibby (DK); Ole Cai Hansen, Værløse (DK); Flemming Jørgensen, Lyngby (DK)

(73) Assignee: Arla Foods Amba, Viby (DK)

( * ) Notice: Subject to any disclaimer, the term of this patent is extended or adjusted under 35 U.S.C. 154(b) by 382 days.

(21) Appl. No.: 10/194,295

(22) Filed: Jul. 15, 2002

(65) Prior Publication Data

US 2003/0022844 A1 Jan. 30, 2003

Related U.S. Application Data

(63) Continuation-in-part of application No. 09/905,108, filed on Jul. 16, 2001.

(60) Provisional application No. 60/305,155, filed on Jul. 16, 2001.

(30) Foreign Application Priority Data

Jul. 16, 2001 (DK) ........................................ 2001 01114

(51) Int. Cl.
*C12P 19/24* (2006.01)
*C12P 19/02* (2006.01)

(52) U.S. Cl. ......................................... 435/94; 435/105
(58) Field of Classification Search .................. 435/94, 435/105

See application file for complete search history.

(56) References Cited

U.S. PATENT DOCUMENTS

| | | | |
|---|---|---|---|
| 4,786,722 A | 11/1988 | Zehner ........................ | 536/1.1 |
| 5,002,612 A | 3/1991 | Beadle et al. ............... | 127/46.1 |
| 5,078,796 A | 1/1992 | Beadle et al. ............... | 127/46.1 |
| 5,356,879 A | 10/1994 | Zehner et al. ................. | 514/25 |
| 5,447,917 A | 9/1995 | Zehner et al. ................. | 514/23 |
| 6,057,135 A | 5/2000 | Ibrahim et al. ............. | 435/105 |

FOREIGN PATENT DOCUMENTS

| | | |
|---|---|---|
| EP | 0 176 971 A2 | 4/1986 |
| EP | 0 237 442 | 9/1987 |
| EP | 0 272 095 | 6/1988 |
| EP | 0 807 682 A2 | 11/1997 |
| GB | 1 497 888 | 1/1978 |
| GB | 1 538 553 | 1/1979 |
| JP | 52-5706 | 1/1977 |
| JP | 56-154991 | 11/1981 |
| JP | 61-81788 | 4/1986 |
| JP | 63-301794 | 12/1988 |
| JP | 06-113875 | 4/1994 |
| JP | 06-339338 | 12/1994 |
| JP | 10-052274 | 2/1998 |
| JP | 10-155480 | 6/1998 |
| WO | WO 99/40217 | 8/1999 |
| WO | WO 00/31287 | 6/2000 |
| WO | WO 01/12834 A1 | 2/2001 |
| WO | WO 03/008593 A2 | 1/2003 |

OTHER PUBLICATIONS

Cubellis, M.V., et al. (1990) Gene 94, 89–94.*
Dion, Michel et al., "Cloning and Expression of a β-glycosidase Gene from *Thermus Thermophilus*, Sequence and Biochemical Characterization of the Encoded Enzyme," Glycoconjugate Journal 16, pp. 27–37 (1999).
Gräbnitz, Folke et al., "Structure of the β-glucosidase Gene bg1A *Clostridium Thermocellum*Sequence Analysis Reveals a Superfamily of Cellulases and β-Glycosidases Including Human Lactose/Phlorizin Hydrolase," European Jounral of Biochemstry, vol. 200, pp. 301–309 (1999).
Lebbink, Joyce H.G. et al., "Improving low–Temperture Catalysis in the Hyperthermostable *Pyrrococoocus Furiosus* β–Glucosides CelB by Directed Evolution," vol. 39, pp. 3656–3665 (2000), Molecular Genetics, Microbiology and Virology, No. 2, pp. 34–40 (1997).
Moracci, Marco et al., "β–Glycosidase from *Sulfolobus Solfetaricus*, "Methods in Enzymology, vol. 330, pp. 201–215 (2001).
Ohtsu, Naomi et al., "Thermostable β–Galactosides from an Extreme Thermophile, *Thermus* sp. A4: Enzyme Purificaition and Characterization, and Gene Cloning and Sequencing," Biosci. Biotechnol. Biochem, vol. 62, No. 8, (1998), pp. 1539–1545.
Patrick, James W. et al., "Coordination of Enzyme Synthesis in the L–Arabinose Operon in *Escherichia Coli*," The Journal of Biological Chemistry, vol. 246, No. 16, pp. 5102–5106 (1971).
Petzelbauer, Inge et al., "Development of an Ultra–High–Temperature Process for the Enzymatric Hydrolysis of Lactose: II. Oligosaccharide Formation by Two Thermostable β–Glycosidases," Biotechnology and Bioengineering, vol. 69, No. 2, pp. 140–149 (2000).
Roh, Hoe J. et al., "Bioconversion of D–galactose into D–tagatose by Expression of L–arabinose Isomerase," Biotechnol. Appl. Biochem., vol. 31, Pt. 1, pp. 1–4 (2000).
Sá–Nogueira, Isabel et al., "The Bacillus Subtilis L–Arabinose (Ara) Operon: Nucleotide Sequence, Genetic Organization and Expression," Microbiology, vol. 143, pp. 957–969 (1997).
English translation of Japanese Office Action dated Jun. 28, 2005 for Application No. 2003–514933.

* cited by examiner

*Primary Examiner*—Charles L. Patterson, Jr.
(74) *Attorney, Agent, or Firm*—Finnegan, Henderson, Farabow, Garrett & Dunner, L.L.P.

(57) ABSTRACT

Tagatose is manufactured by hydrolyzing lactose to galactose and glucose and isomerizing galactose to tagatose and chromatographic separation and recycling any unconverted compounds. Thereby high yields of pure tagatose are obtained.

18 Claims, 4 Drawing Sheets

Fraction 1: gal 20% dm

Fraction 2: tag

Fraction 3: glu

Fraction 1: gal 20% dm

Fraction 2: tag

Fraction 3: glu

PROCESS FOR MANUFACTURING OF TAGATOSE

This application is a Continuation-In-Part of U.S. application Ser. No. 09/905,108, filed Jul. 16, 2001, in the name of Flemming JØRGENSEN et al., and claims the benefit of provisional application No. 60/305,155, filed Jul. 16, 2001, the contents of both which are incorporated herein by reference.

TECHNICAL FIELD OF THE INVENTION

The present invention concerns enzymatic manufacturing of tagatose, especially D-tagatose.

BACKGROUND OF THE INVENTION

D-Tagatose is a multi-purpose low-calorie bulk sweetener having non-cariogenic and prebiotic properties. D-Tagatose can be used in food and functional food as well as in pharmaceuticals, cf. U.S. Pat. No. 4,786,722, U.S. Pat. No. 5,356,879 and U.S. Pat. No. 5,447,917.

According to U.S. Pat. No. 5,002,612 and U.S. Pat. No. 5,078,796 D-tagatose has been manufactured by hydrolyzing lactose or a lactose containing material to a mixture of galactose and glucose using a lactase, optionally removing glucose followed by chemical isomerization of galactose to tagatose.

U.S. Pat. No. 6,057,135 describes manufacturing of D-tagatose from cheese whey or milk, which is hydrolyzed to prepare a mixture of galactose and glucose. Glucose is separated from the galactose by fermentation of glucose and subjected to isomerization using L-arabinose isomerase.

SUMMARY OF THE INVENTION

In a first aspect of the invention a process is provided for manufacturing of tagatose comprising a) hydrolyzing lactose or a lactose containing starting material to obtain galactose and glucose, b) isomerizing the obtained galactose with a L-arabinose isomerase, and c) chromatographic separation of products and unconverted compounds and recycling of unconverted compounds to the process.

In a second aspect of the invention a process is provided, wherein steps a) and b) are performed in one reactor.

In a further aspect of the invention a process is provided for manufacturing of D-tagatose.

In a still further aspect of the invention a process is provided, wherein the L-arabinose isomerase used in step b) is thermophilic.

In a still further aspect of the invention a process is provided, wherein the lactase used in step a) is thermophilic.

In a still further aspect of the invention a process is provided, wherein the temperature used in step(s) a) and/or b) is/are 40–90° C.

Still further aspects of the invention are given in the appended claims.

DETAILED DESCRIPTION OF THE INVENTION

Figure 1:
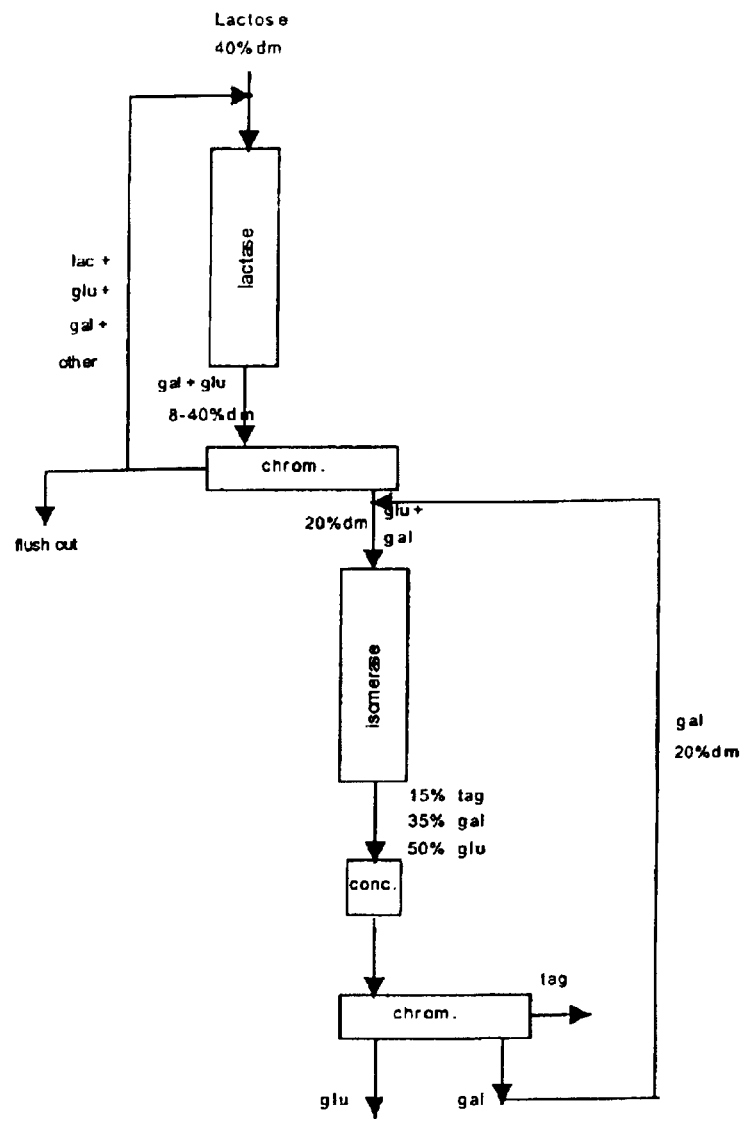
FIG. 1 shows the process of example 1 schematically.
Figure 2:
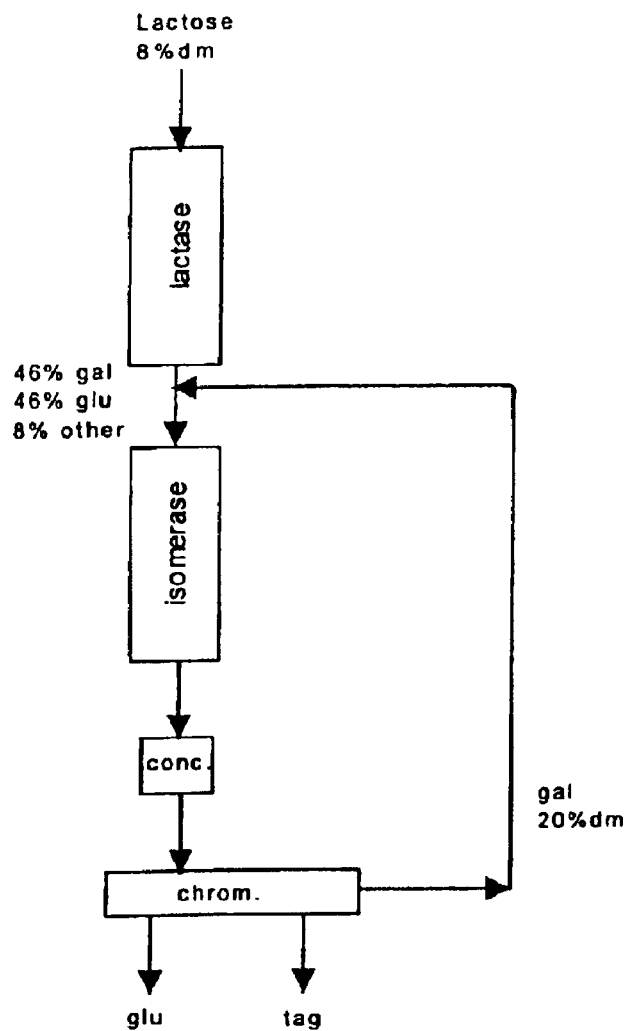
FIG. 2 shows the process of example 2 schematically.
Figure 3:
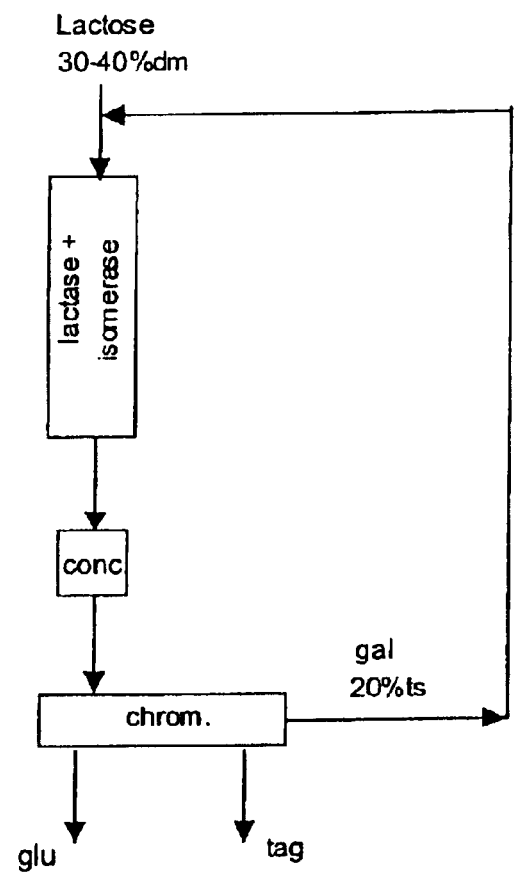
FIG. 3 shows the process of example 3 schematically.

It has surprisingly been found that it is possible to use chromatographic separation and recycling in an enzymatic process for manufacturing of tagatose. Thereby higher yields and a cleaner process are achieved. The total yield as well as the yield for each cycle are higher.

Using this process it is possible to recycle and use any unconverted lactose and galactose. It is also possible to separate the products, tagatose and any by-products, especially glucose from galactose and use the glucose for other purposes.

The starting material can be any lactose or lactose containing material.

Lactose is a by-product from the cheese manufacture. This process gives an opportunity to convert lactose, a low-value product produced in excess, into a high value product with properties beneficial to humans. This is a way to use lactose. Opportunities for the utilization of lactose have been sought for a long period of time.

The process involves enzymatic hydrolysis of lactose, enzymatic conversion of galactose into tagatose and optionally chromatographic separation with recycling of non-converted products.

The consumption of chemicals etc is low.

The production of bi-products is low. Only one by-product is produced, viz. glucose as a glucose syrup/powder, which can be used for food.

It is possible to perform the entire reaction in one reactor containing enzymes for the hydrolysis of lactose as well as the isomerization of galactose. Thereby step a) and step b) are combined.

In so doing the complete process is improved in respect of yield per time unit. Galactose is continuously removed from the reactor by isomerization thereof to tagatose, thus reducing the concentration of galactose that would otherwise impede lactase and result in restraint of the transformation of lactose to galactose and glucose. It is possible to carry out the process at high concentration (Brix) because of the high process temperature. Evaporation capacity will be saved which again will result in improved economy as regards investment and working. The increased sugar concentration moreover has the effect that the use of preservatives can be reduced. Also the first chromatographic separation will become superfluous which again means improved economy as regards investment and running.

Especially an enzymatic conversion of lactose to glucose and galactose with subsequent isomerization of the galactose to tagatose in the same enzyme reactor has been demonstrated. The initial tests confirmed that LacS lactase enzyme and L-arabinose isomerase from *T. mathranii* could function under identical metal ion, buffer and temperature conditions. The principle was then tested by incubation of an 800 mM lactose solution (28%) with immobilized lactase and immobilized isomerase. Samples were analyzed for contents of lactose, glucose, galactose and tagatose by HPLC. During 24 hours of incubation the concentration of glucose increased to about 800 mM indicating that all lactose was cleaved. The concentrations of galactose and tagatose both increased linearly to about 300 mM. Consequently the degree of conversion was $(300/800) \times 100\% = 38\%$.

The further enzyme can be introduced into the same reactor, a so-called combi-reactor.

The tagatose is especially D-tagatose, which is in high demand in the food industry.

All lactases can be used in step a). Examples are enzymes derived from the group consisting of *Bacillus, Sulfolobus, Thermoanaerobacter, Thermus* and *Pyrococcus*.

All L-arabinose isomerases can be used in step b). Examples are enzymes derived from the group consisting of *Bacillus, Sulfolobus, Thermoanaerobacter* and *Thermotoga*.

The enzymes can be used in any form. For example is it possible to use immobilized enzymes.

Biotechnological Institute, Denmark, can deliver usable lactases and L-arabinose-isomerases.

Biotechnological Institute, Denmark found and tested an enzyme derived from *Thermoanaerobacter mathranii, Thermoanaerobacter mathranii* DSM 11426. They have filed U.S. patent application Ser. No. 09/905,108 covering their invention.

$K_m$ values for *T. mathranii* enzyme on D-galactose are lower than values for enzymes from common L-arabinose isomerase producing organisms, such as *Aerobacter aerogenes, Bacillus amyloliquefaciens, Arthrobacter* sp, and *Lactobacillus pentosus*. Therefore *T. mathranii* has a better affinity.

This last mentioned enzyme is thermophilic.

An added benefit of using thermophilic enzymes is the possibility of using high process temperature where the solubility of lactose and glucose is higher. This means that more concentrated products can be used for the enzymatic process of the invention. This again means a less water consumption and less water for evaporation. This will give technical advantages and less need for water and energy i.a. for heating and cooling process streams.

The use of thermophilic enzymes has further made it possible to work at a higher temperature. This leads to a better hygiene because of reduced risk of contamination with damaging microorganisms. Furthermore an increased conversion of galactose to tagatose is achieved at higher temperatures compared to the conversion of arabinose to ribulose. In addition hereto there may also be technical advantages such as easier flow and quicker filtration.

It is thus preferred to use enzymes having optimal yields at high temperatures in steps a) and/or in step b). This will normally give a faster reaction. Further, it is possible to clean the system using high temperatures, for example pasteurization temperatures usually used in the dairy industry or temperatures over 100° C., if the enzymes are thermophilic or even extremophilic. If there is no or only minor temperature difference between the temperature in steps a) and b), the energy for cooling and heating is reduced. The production process can thus be run at temperatures above 60° C. This has wide implications for the microbiology and the consumption of steam and brine for warming and cooling.

The temperature used in step(s) a) and/or b) is/are 40–90° C. Normally it is 60–90° C. Preferably the temperature is 60–80° C., more preferably 65–70° C., and the most preferred temperature is 65° C. However, the temperature will depend of the chosen enzymes, and it can be different in steps a) and b). As mentioned above, some advantages are achieved by using the same temperature in both steps, including performing both steps simultaneously in one reactor.

Contrary to chemical conversion of galactose into tagatose the process can be run at a pH value optimal for sugars. This significantly reduces the production of sugar degradation products. As a result, recovery and economy are improved. A typical pH value is about 7.0. Usable pH values and other reaction parameters are i.a. found in U.S. Pat. No. 6,057,135. Yamanaka, K and Wood, W. A. (1966) *Methods in Enzymology* 9: 596–602, list a number of lactic acid bacteria providing an L-arabinose isomerase enzyme capable of producing ketoses from i.a. D-galactose.

The product of the invention in the form of syrup is so pure that it is possible to use tagatose syrups directly. Hitherto it has been necessary to purify the product, for example to crystallize the impure syrup and dissolve or solubilize it again.

As mentioned above, D-Tagatose can be manufactured from a lactose-containing source (e.g. cheese whey, casein whey or milk). Lactose is hydrolyzed to equal amounts of galactose and glucose by the lactase, which can be immobilized lactase.

Galactose is preferably separated from glucose by chromatography. Non-hydrolyzed lactose may be separated and recycled to the enzyme column. Galactose is isomerized to tagatose by optionally immobilized L-arabinose isomerase. Non-isomerized galactose may be separated by chromatography and recycled. The fraction containing D-Tagatose is crystallized. The crystals are separated from the mother liquor and dried. The mother liquor high in tagatose may be recycled/recrystallized. It is also possible to directly use the tagatose produced as syrup in food products for humans or other purposes.

Thus, there has now been found an effective enzymatic procedure combined with chromatography for manufacturing of tagatose in high yield and in a very pure form in one or two reactors. The process has special advantages if performed with thermophilic/extremophilic enzymes.

The new process for the production of tagatose is highly effective and clean due to a specific enzymatic conversion combined with recycling of non-converted products. The process is extremely effective and environmentally friendly.

EXAMPLES

Example 1

Hydrolysis of Lactose with Recirculation
Isomerization of Galactose with Recirculation 1. Lactose is produced from whey by ultrafiltration followed by crystallization.
2. A solution of lactose in water (8–40% DS) is hydrolyzed by immobilized lactase at high or low temperature (either by enzyme from *Aspergillus oryzae* or a thermophilic organism).
3. Glucose and galactose are separated by chromatography. Depending on concentration of feed it may be necessary to concentrate for instance by evaporation.
4. Lactose and possible galactooligosaccharides are recycled to the column containing immobilized enzyme.
5. If the concentration of oligosaccharides in the recycling loop is too high (the hydrolysis is undesirably affected), the system is flushed.
6. The fraction containing glucose and galactose is isomerized by immobilized galactose isomerase (from a thermophilic organism)
7. The mixture is concentrated for instance by evaporation
8. Tagatose is separated by chromatography
9. The tagatose fraction is concentrated and possibly crystallized
10. The glucose fraction might be concentrated for sale as a syrup or it may be further processed
11. The Galactose fraction is recycled to the isomerase column Example 2

Hydrolysis of Lactose without Recirculation with Following Isomerization

1. Lactose is produced from whey by ultrafiltration followed by crystallization.

2. A solution of lactose in water (8–40% DS) is hydrolyzed by immobilized lactase (the enzyme originates from *Aspergillus oryzae*).
3. The mixture containing about 46% of glucose, 46% of galactose is passed through a column containing immobilized galactose isomerase (from a thermophilic organism). About 30% of galactose is converted into tagatose.
4. The product is separated into 3 fractions by concentration and chromatographic separation:
   Fraction 1 contains mainly non-converted galactose. This fraction is recycled to the galactose isomerase column
   Fraction 2 contains mainly tagatose. This fraction is concentrated for crystallization or it is marketed as syrup.
   Fraction 3 contains mainly glucose, but also galactooligosaccharides produced by the lactase enzyme as well as un-converted lactose. This fraction is concentrated for sale as syrup or for further processing, such as crystallization or drying.

Example 3
Hydrolysis and Isomerization in one Reactor
1. Lactose is produced from whey by ultrafiltration followed by crystallization.
2. A solution of lactose in water is passed through a column containing immobilized lactase and L-arabinose isomerase (both enzymes originating from thermophilic organisms).
3. The product is separated into 3 fractions by concentration and chromatographic separation:
   Fraction 1 contains mainly non-converted galactose. This fraction is recycled to the column for enzymatic conversion.
   Fraction 2 contains mainly tagatose. This fraction is concentrated for crystallization or it is marketed as a syrup.
   Fraction 3 contains mainly glucose, but also galactooligosaccharides produced by the lactase enzyme as well as un-converted lactose. This fraction is concentrated for sale as a syrup or for further processing, such as crystallization or drying Example 4
One-Reactor Conversion of Lactose to Tagatose with Immobilized Lactase and Immobilized Isomerase The β-glycosidase encoding gene from *Sulfolobus solfataricus* (Moracci M, Ciaramella M, and Rossi M. [2001] Methods in Enzymology vol. 330, p. 201–15) was cloned and expressed in *E. coli*. The gene was isolated by polymerase chain reaction (PCR) using purified chromosomal DNA from *Sulfolobus solfataricus* strain P2. Primers containing additional restriction sites for NdeI and BamHI were designed to yield the entire coding sequence on a fragment which was subsequently cloned into the standard expression plasmid pET3a (Novagen).

*E. coli* cells expressing the enzyme were cultivated, harvested by centrifugation, lysed in a French pressure cell and cross-linked with glutaraldehyde and polyethylenimine as described in U.S. Pat. No. 4,354,105. The immobilized enzyme was recovered by centrifugation and lyophilisation of the pellet. The activity of the immobilized lactase was 1500 units/g dry weight. One unit was defined as the amount of enzyme liberating one micromole of glucose per min at 65° C., pH 7, in a 30-% (w/v) solution of lactose.

The L-arabinose isomerase gene from *Thermoanaerobacter mathranii* was cloned and expressed in *E. coli* as described in patent application no. U.S. Ser. No. 09/905,108 (Biotechnological Institute, Denmark).

*E. coli* cells expressing the enzyme were cultivated, harvested by centrifugation, lysed in a French pressure cell and cross-linked with glutaraldehyde and polyethylenimine as described in U.S. Pat. No. 4,354,105. The immobilized enzyme was recovered by centrifugation and lyophilisation of the pellet. The activity of the immobilized L-arabinose isomerase was 50 units/g dry weight. One unit was defined as the amount of enzyme producing one micromole of D-tagatose per min at 65° C., pH 7, in a 30-% (w/v) solution of D-galactose.

One-milliliter assay mixtures containing 20 mg of immobilized lactase, 80 mg of immobilized isomerase, 0.30 g of lactose (30%, 875 mM), 25 mM K-maleate buffer, pH 6.9, and 5 mM $MnCl_2$ were incubated at 65° C. A control sample without enzymes was treated similarly. Periodically, samples were taken and the concentrations of glucose, galactose and tagatose were determined by high pressure liquid chromatography using an Aminex HPX-87C column (Bio-Rad) and a refractive index detector (Waters 410). The mobile phase was de-ionized, degassed water, the column temperature was 85° C., and the flow rate was 0.6 ml/min.

Figure 4:
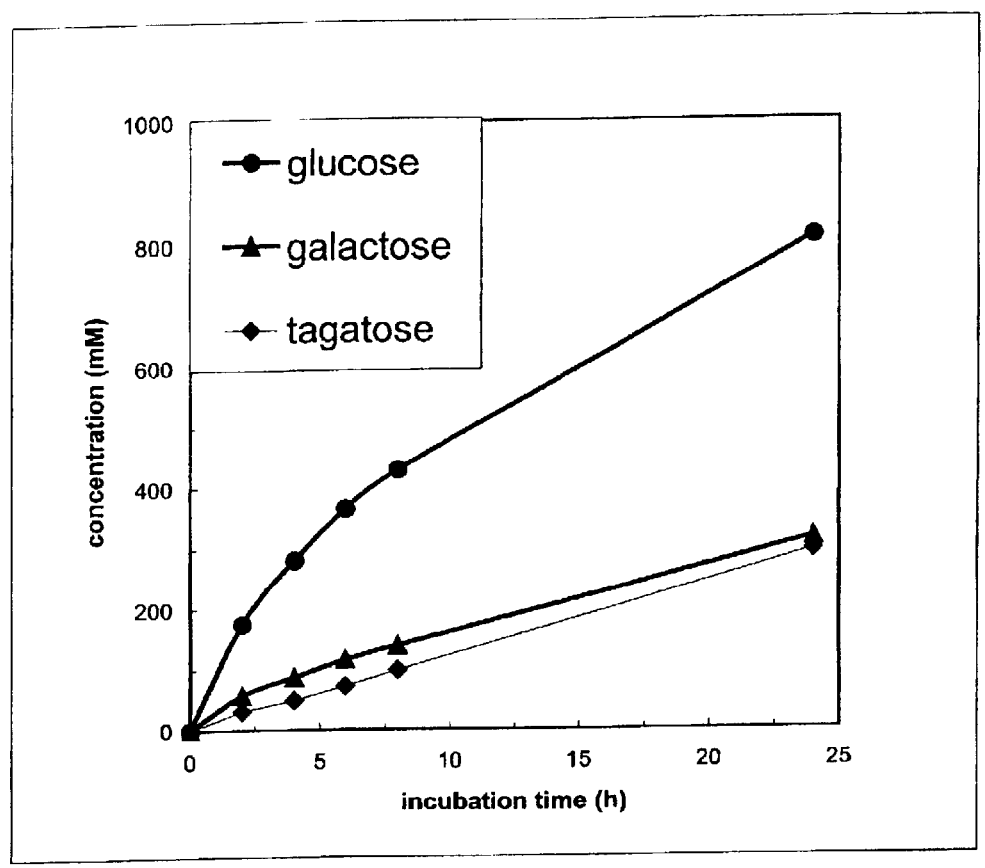
FIG. 4 shows the result of example 4.

As shown in FIG. 4, the concentration of glucose increased to about 800 mM over 24 h, indicating that almost all lactose was hydrolyzed to galactose and glucose. The concentration of tagatose increased linearly to about 300 mM over 24 h, indicating a bioconversion of 300 mM/800 mM=38%.

TABLE

Conversion of lactose to tagatose with immobilized lacS lactase from *S. solfataricus* and araA isomerase from *T. mathranii*

| incubation time (h) | lactose (mM) | glucose (mM) | galactose (mM) | tagatose (mM) |
| --- | --- | --- | --- | --- |
| 0 | 816 | 0 | 0 | 0 |
| 2 |  | 176 | 57 | 30 |
| 4 |  | 281 | 87 | 48 |
| 6 |  | 366 | 116 | 72 |
| 8 |  | 430 | 139 | 98 |
| 24 |  | 811 | 316 | 295 |

What is claimed is:
1. A process for manufacturing of tagatose comprising
   a) hydrolyzing lactose or a lactose containing starting material with a lactase to obtain galactose and glucose
   b) isomerizing the obtained galactose in the presence of glucose with a L-arabinose isomerase to obtain tagatose, and
   c) separating by chromatography products and unconverted compounds and recycling of unconverted compounds to the process.
2. A process of claim 1, wherein unconverted lactose is separated by chromatography and recycled to step a) for hydrolysis.
3. A process of claim 1, wherein unconverted galactose is separated by chromatography and recycled to step b) for isomerization.
4. A process of claim 1, wherein step a) and step b) are performed in one reactor.
5. A process of claim 1, wherein the galactose is D-galactose and the tagatose is D-tagatose.
6. A process of claim 1, wherein the L-arabinose isomerase used in step b) is thermophilic.
7. A process of claim 1, wherein the lactase used in step a) is thermophilic.

8. A process of claim 1 or 2 wherein the L-arabinose isomerase used in step b) is derived from *Bacillus, Sulfolobus, Thermoanaerobacter* or *Thermotoga*.

9. A process of claim 8, wherein the L-arabinose isomerase is derived from *Thermoanaerobacter mathranii*.

10. A process of claim 9 wherein the L-arabinose isomerase is derived from *Thermoanaerobacter mathranii* DSM 11426.

11. A process of claim 1, wherein the lactase used in step a) is derived from *Bacillus, Sulfolobus, Thermoanaerobacter, Thermus* or *Pyrococcus*.

12. A process of claim 1, wherein one or more of the enzymes used is immobilized.

13. A process of claim 1, wherein the temperature used in step(s) a) and/or b) is/are 40–90° C.

14. A process of claim 13, wherein the temperature is/are 60–90° C.

15. A process of claim 14, wherein the temperature is/are 60–80° C.

16. A process of any one of claims 1–3, wherein the temperature used in step(s) a) and/or b) is/are 65–70° C.

17. A process of claim 16, wherein the temperature is/are 65° C.

18. A process according to claim 4, wherein the L-arabinose isomerase used is derived from *Thermoanaerobacter mathranii* and the lactase used is derived from *Sulfolobus solfataricus*.

* * * * *